US010281450B2

(12) United States Patent
Pileggi

(10) Patent No.: US 10,281,450 B2
(45) Date of Patent: May 7, 2019

(54) UNIVERSAL MACHINE FOR RHEOLOGICAL AND MECHANICAL TESTS

(71) Applicant: Gisele Castro Fontanella Pileggi, Sao Paulo (BR)

(72) Inventor: Gisele Castro Fontanella Pileggi, Sao Paulo (BR)

( * ) Notice: Subject to any disclaimer, the term of this patent is extended or adjusted under 35 U.S.C. 154(b) by 69 days.

(21) Appl. No.: 15/321,555

(22) PCT Filed: Jun. 23, 2015

(86) PCT No.: PCT/IB2015/054713
§ 371 (c)(1),
(2) Date: Dec. 22, 2016

(87) PCT Pub. No.: WO2015/198230
PCT Pub. Date: Dec. 30, 2015

(65) Prior Publication Data
US 2017/0212025 A1    Jul. 27, 2017

(30) Foreign Application Priority Data

Jun. 24, 2014    (BR) ............................ 102014015604

(51) Int. Cl.
*G01N 11/14* (2006.01)
*G01N 33/38* (2006.01)
*G01N 11/00* (2006.01)

(52) U.S. Cl.
CPC ........... *G01N 33/383* (2013.01); *G01N 11/14* (2013.01); *G01N 2011/0026* (2013.01)

(58) Field of Classification Search
CPC ........ G01N 11/08; G01N 11/14; G01N 11/10; G01N 3/08; G05B 13/0255; G05B 17/02
See application file for complete search history.

(56) References Cited

U.S. PATENT DOCUMENTS 4,316,383 A * 2/1982 Fruman ................. G01N 11/08
    73/54.09
5,456,105 A * 10/1995 James .................... G01N 11/12
    73/54.01

(Continued)

OTHER PUBLICATIONS

International Search Report dated Dec. 23, 2015 for related PCT patent app. No. PCT/2015/054713.

(Continued)

*Primary Examiner* — Lisa M Caputo
*Assistant Examiner* — Brandi N Hopkins
(74) *Attorney, Agent, or Firm* — D'Ambrosio & Menon, PLLC; Usha Menon

(57) ABSTRACT

An universal machine is comprised of the arrangement of a set of modules (CM) that make up means of rheological and mechanical tests for the assessment of longitudinal forces perpendicular to the rotation direction of an alternate current servomotor. Its modules are comprised of: a) structural organization; b) electronic components cabinet of the electronics system (St)/(Sw); c) dry gear reducer; d) alternate current servomotor; e) fast coupling system for changing geometries; f) test containers, as well as devices for the execution of materials in hardened state; g) load cell device for recording regular longitudinal forces. The machine provides the interconnection with a data processing system (PC) and the aforementioned modules (CM) are controlled by a specific electronic system (St) for speed control, torque control and rotation direction.

11 Claims, 15 Drawing Sheets

(56) References Cited

U.S. PATENT DOCUMENTS

| | | | |
|---|---|---|---|
| 5,771,211 A * | 6/1998 | Tanase | G11B 11/10506 |
| | | | 369/13.5 |
| 5,777,212 A * | 7/1998 | Sekiguchi | G01N 11/162 |
| | | | 73/54.33 |
| 5,900,539 A * | 5/1999 | Tremblay | G01N 11/04 |
| | | | 73/54.11 |
| 6,649,095 B2 | 11/2003 | Buja | |
| 6,804,563 B1 | 10/2004 | Lafaye De Micheaux | |
| 7,049,147 B2 * | 5/2006 | Sentmanat | G01N 11/165 |
| | | | 436/180 |
| 7,233,834 B2 | 6/2007 | McDonald, Jr. et al. | |
| 7,770,436 B2 | 8/2010 | Baek | |
| 2007/0193234 A1 | 8/2007 | Fox et al. | |

OTHER PUBLICATIONS

"Measurement of the Rheological Properties of Cement Paste;" The National Institute of Standards and Technology Ferraris. C. 1998.
"Testing and Modeling of Fresh Concrete Rheology;" National Institute of Standards and Technology; Ferraris, C. and Larrard, F. Feb. 1998.

* cited by examiner

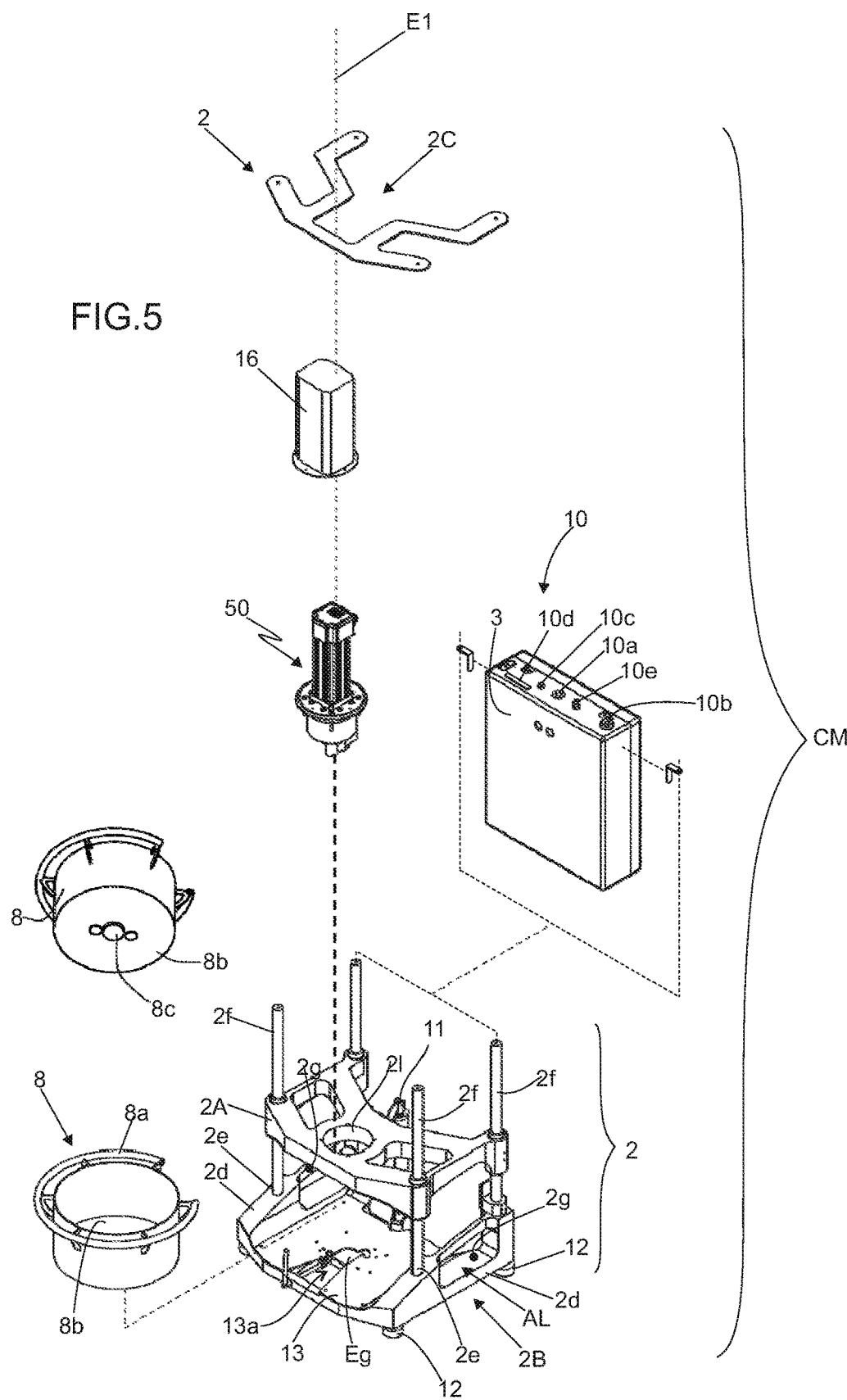

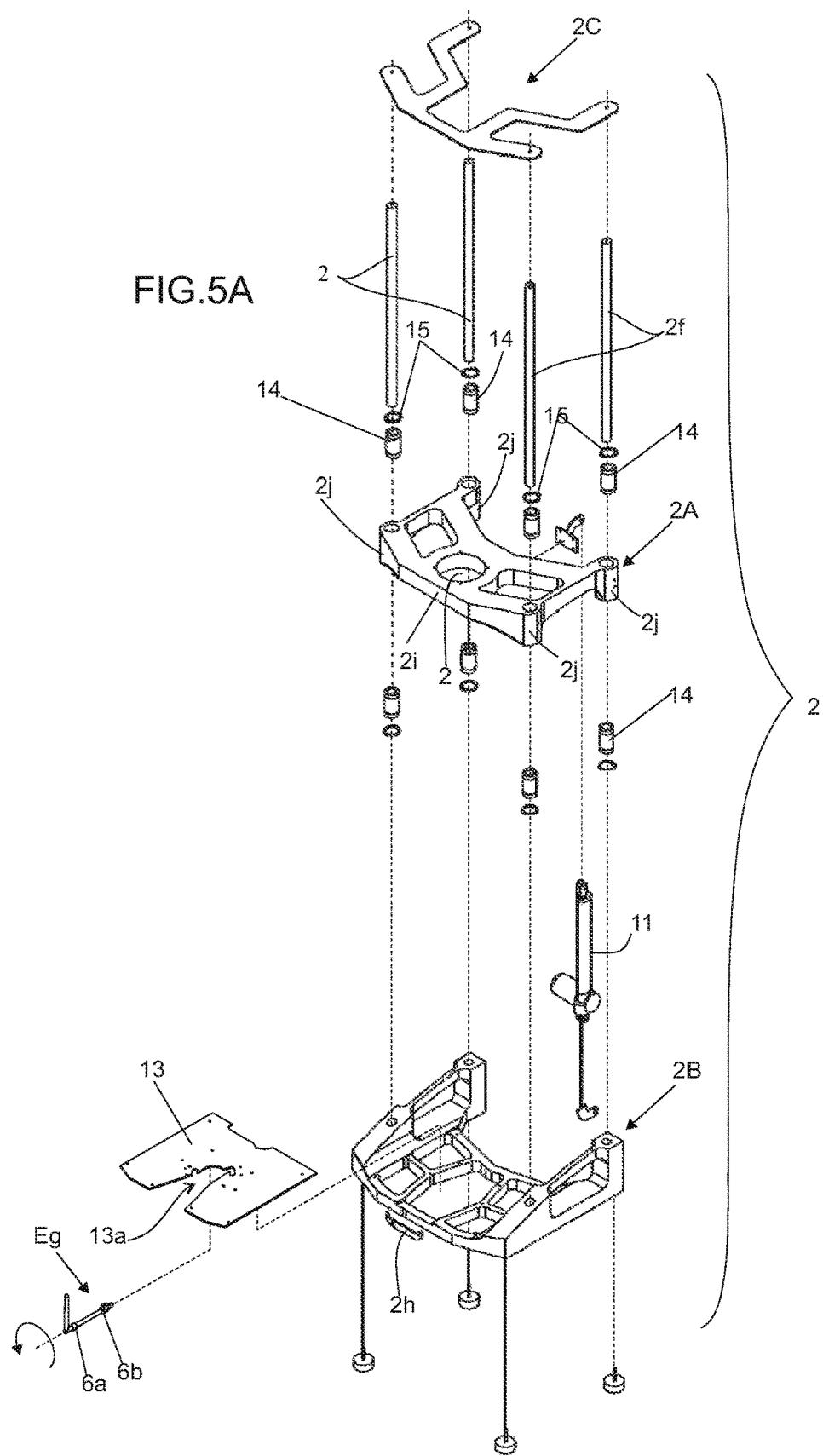

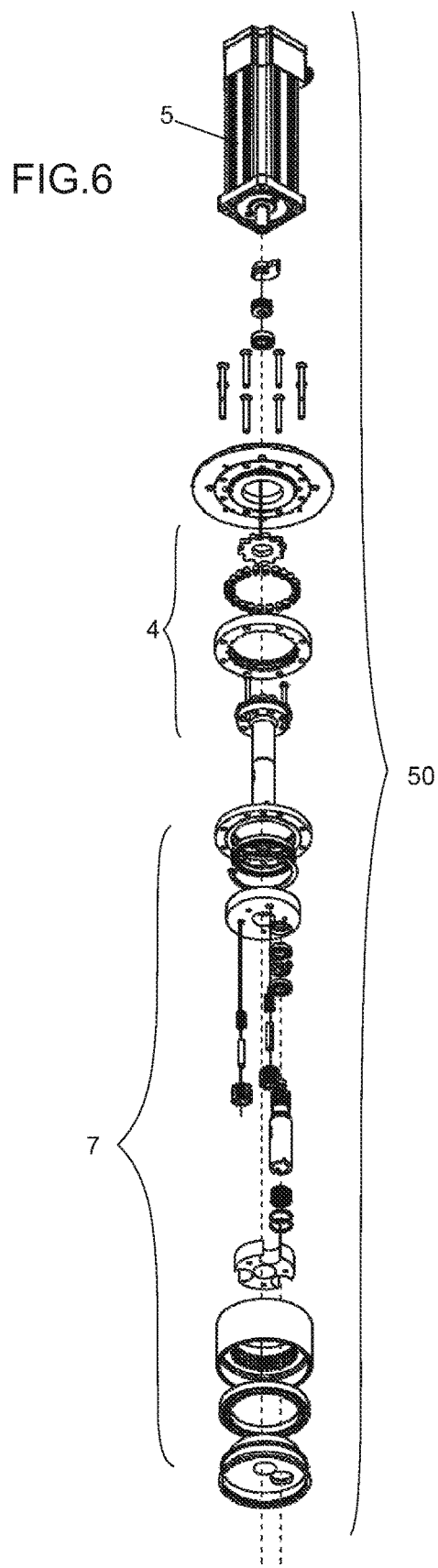

FIG.14
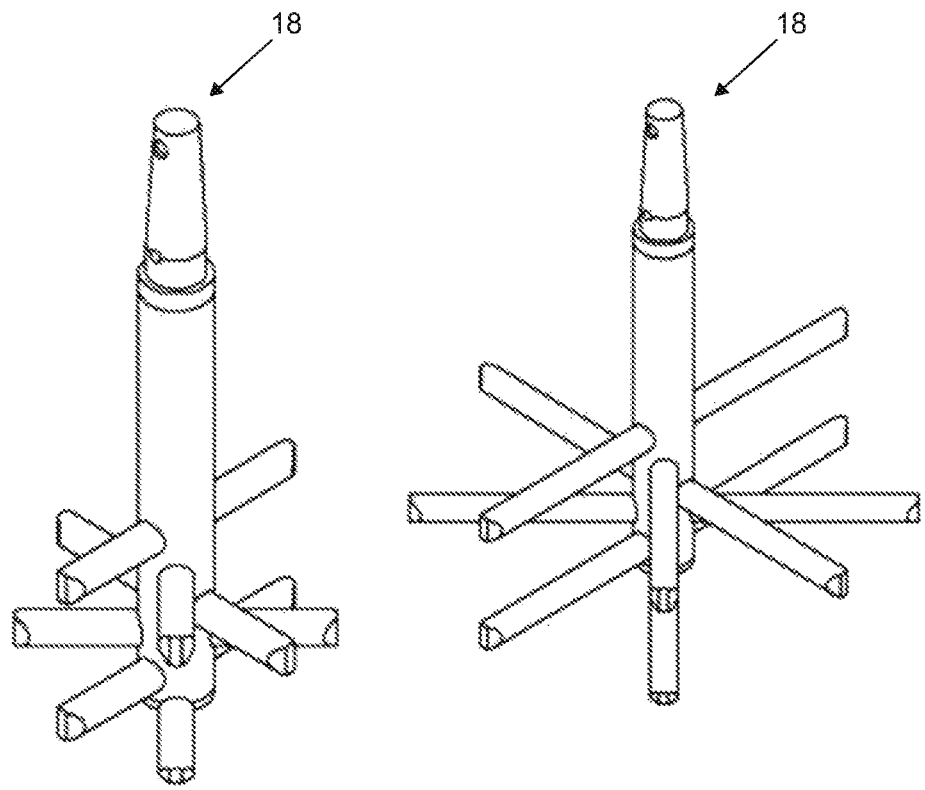
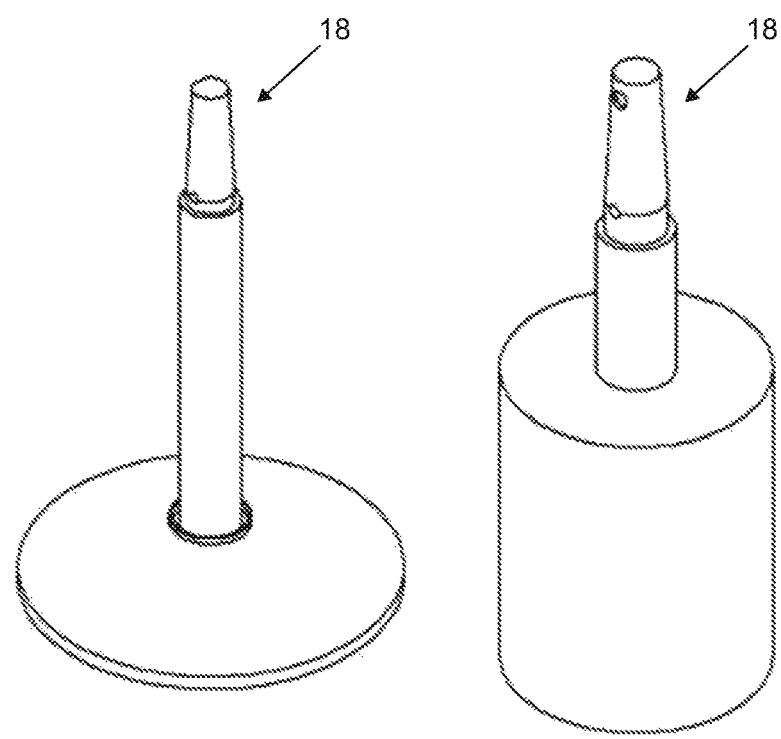

UNIVERSAL MACHINE FOR RHEOLOGICAL AND MECHANICAL TESTS

FIELD OF APPLICATION

The current invention patent is a universal machine of rheological and mechanical tests for modular tests of cementitious materials, such as mining, asphaltic, polymeric, food, pharmaceutical, cosmetic materials, etc., with the aforementioned machine being comprised of distinct modules that allow the investigation of mixture behavior, prediction of fluid state characteristics and consolidation of inert or reactive heterogeneous multiphase systems, with or without the presence of liquid phase and with elevated granulometric extension.

TECHNICAL BACKGROUND

It is known that heterogeneous suspensions are characteristically composed of different phases in their formulation, more explicitly, and can be the result of the combination of liquids with solid particles, which can vary from millimeters to submicrons in size. These suspensions also contemplate the combination of different immiscible fluids, constituting emulsions in the system liquid phase, with the possibility of also including air bubbles in the system.

These heterogeneous suspensions are present in different technological areas, such as building materials as concretes, mortars, fibrocement, prefabricated components, etc., soils, foods, cosmetic and mining products, etc.

One major difficulty involved with materials of such nature is related to the assessment of the behavior of these materials in fluid state, even to those that will be transformed into solids at some other processing stage.

The techniques for assessing the behavior of fluids in shear stress, known as rheological characterization techniques, have as their basic principle the submission of these fluids to controlled stresses or deformations. Countless methods described in the literature are classified into four categories according to the flow measurement or shear stress measurement procedure, which are:

Free flow tests—the material flows due to its own weight, without any confining, or an object penetrates the material as the result of gravitational force;

Confined flow tests—the material flows due to its own weight or under the application of pressure by means of a restricted orifice;

Vibration tests—the material flows due to the application of vibration;

Shear tests under rotational flow the material is submitted to rotational shearing in a parallel plate or concentric cylinders system Another way of classifying the test methods is related to the shearing range in which the materials being analyzed are submitted, given that in practice two major test classes can be pointed: single point and multipoint.

The single point category encompasses the most of traditional tests employed in the control of concretes consistency, as indicated in Table 1, besides the Vane test—Amziane et al., 2005.

Table 1 contains the main methods for rheological characterization of fresh concrete, based on the classification given by "Nist"—Koehler & Fowler Koehler & Fowler, 2003.

TABLE 1

| NIST Classification | Test | Parameters | Type of measurement |
| --- | --- | --- | --- |
| Free flow | Truncated cone | Yield Strength | single point |
| Free flow | Modified truncated cone | Yield Strength; | single point |
| Confined Flow | Orimet Test V-Funnel Test | Viscosity | single point |
| Confined Flow | Ability Filling | Viscosity | single point |
| Vibration | Powers Remolding Test | Viscosity | single point |
| Rotational Rheometer | Rheometers | Yield Strength; Viscosity | multipoint |

Generally speaking, these tests characterize the materials in a single strength or shear rate condition. In the free and confined flow tests, the strength applied is proportional to the density of the material, while in the vibration tests, the shear rate applied is defined by the frequency and amplitude of the mobile element. In turn, the Vane test is a test that quantifies the yield strength of compositions.

Results obtained by means of such methods do not provide, therefore, a complete rheological characterization of concretes, with the possibility of resulting in wrong interpretations about the behavior of concretes in fluid state, under different application conditions.

Illustrating this concept, the FIG. 1 presents a schematic representation of three distinct "Bingham" fluids. The schematic describes the strength vs. shear rate profiles and the figures below the respective viscosities calculated as the ratio between strength and shear rate.

Table 1 presents the main rheological characterization methods according to the "NIST" classification, identifying the fundamental rheological parameters to which the test is related. The aforementioned presents, still, a second form of classification of these methods, based on the quantity of shear rates assessed during the single point and multipoint tests.

As observed, the 'A' and 'B' systems present the same yield strength, but the strength and fluid viscosity levels of 'B' are higher than those of system 'A' at the remaining shear rates.

In FIG. 1 it is verified the 'strength profiles'×'shear rate', where the circles in orange highlight the shear rates with the equivalent viscosities calculated as the strength/shear rate ratio.

Besides the intrinsic uncertainties of the single point characterization concept, the presented test methods do not isolate the fundamental rheological parameters, with exception of the Vane test yield strength test. Overall, these methods provide results that are influenced both by the viscosity as by the materials' yield strength, as demonstrated in FIG. 2 for determination of fluidity by means of the consistency test similar to the truncated cone.

Finite element simulation results confirm that the consistency values present an inversed relation with the two rheological constants, yield strength and viscosity.

As a matter of fact, the rheological assessment of reactive concentrated suspensions with high viscosity, which consistency changes throughout time due to irreversible microstructural changes, in other words, cement hydration, polymerization, coagulation, etc., is a challenge in the field of rheology—Meeten, 2000.

Therefore, the identification of rheological parameters associated to the behavior of fluids and suspensions must be made my means of multipoint techniques that assess the behavior of materials at different shear rates and strengths, as in rheometry tests—Pileggi et al., 2000.

Such multipoint tests consist of the rheological characterization of fluids and suspensions in different conditions of shear strength and rate, enabling thus the simultaneous identification of fundamental rheological parameters, in other words, yield strength, viscosity and rheological profile. These types of tests applied to concretes are predominantly based on rotational rheometry—Ferraris, 1999.

The aforementioned rheometers are pieces of equipment dedicated to the assessment of rheological properties of fluids and suspensions, and allow the study of viscosity and yield strength behaviors as a function of other variables, such as time, temperature, etc.

The various rheometers for suspensions that are commercially available are based on only two basic functioning principles—Stein, 1986, which are: (a) rheometer in which the torque that is proportional to the strength applied to the fluid is controlled, and the resulting shear is assessed; (b) rheometer in which the shearing applied to the material is controlled, and the strength necessary for such is registered. Therefore, it is verified that the torque rheometers are indicated to assessments in which the strength requirements control the flow of material, while the shearing equipment are the most indicated to assessments of the rheological behavior in various flow rates.

Overall, the commercially available precision rheometers are not adequate to materials with an extensive granulometry, such as concretes and mortars, due to the fact that these rheometers can only act in restricted torque ranges, being limited to systems comprised of particles smaller than 100 µm.

Additionally, the commonly employed test geometries: concentric cylinders, parallel plate, cone-plate, capillary, vane, etc., tend to not be adequate to the assessment of concentrated systems or with addition of microparticles, which is the case of concrete and mortars.

It is known that the first rheometer to be specifically developed to the rheological characterization of concretes dates back to the 1960's, where the Powers model—Power, 1968—was based on the concentric cylinders model for the application of shear forces to the material. In this conception, the previously mixed concrete is poured into a cylindrical container in which a rotational element, also cylindrical, is introduced at the center of the mass, and the forces necessary the move the central cylinder are registered.

Therefore, based on this architecture, new models have been developed, such as 'Wallevik' and 'Gjorv' "Con Tec BML viscometer"; 'Cousso' "Cemagref-IMG"; 'Tattersall' and 'Bloomer' "Two-Point rheometer"—Brower, 2001. Besides the aforementioned models, the technological evolution of rheometers resulted in pieces of equipment that use other concepts for sheared material, as the parallel plate system developed by Larrard et. al. "Btrheom" and the planetary system proposed by 'Beaupre' "IBB rheometer"—Ferraris, 1999.

The rheometer for mortars and concretes developed at Poli-USP allows the use of two concepts of shear application: concentration or planetary rotation.

The use of rheometers has gained space, and the paper published in 1998 by the National Institute of Standards and Technology—NIST—'Ferraris and Larrard, 1998' can be highlighted among several others. In this paper, following a bibliographic review about the rheological characterization of construction concrete, it is proposed the use of rheometers for the characterization of high-performance self-yielding concretes.

The importance of using rheometers in the rheological characterization of concretes has been recognized in such manner that in September 2001, NIST published a report related to an international cooperation work carried out between eight countries, called '*Comparison of concrete rheometers*': International tests at LCPC—Nantes, France, 2000—Ferraris & Brower, 2001.

The main purpose of this project consists in comparing, for the first time, the operational performance of distinct rheometers 'Con Tec BML viscometer', 'Cemagref-IMG', 'Two-Point rheometer', 'Btrheom e IBB rheometer', given that, there were no standards and norms for the functioning of such pieces of equipment at the time.

Therefore, the five rheometers were transported from their countries of origin for the Laboratoire central des pants et chaussèes (LCPC) in France, being simultaneously used in the assessment of the behavior of several concrete compositions.

Among the observations contained in the report, the main one was the confirmation that, in spite of the absolute differences between the measured values, the rheometer assess and classify in a similar manner the rheological behavior of distinct concretes, as observed by the yield strength and viscosity in FIG. 3, which provides the conditions for a future establishment of correlation curves between the devices.

In spite of the advantages associated to rheometry, the large dimensions of rheometers of concretes do not allow the portability that is necessary for their use in technological control in construction works, being, therefore, indicated for the development of compositions in laboratories and concrete centers.

This technology gap has been overcome with the arrival of portable rheometers, which consist of simplified, solely dedicated to the execution of standardized control tests in construction works.

One additional advantage of the use of rheometers for the characterization of concretes comes from the fact that the identification of its parameters and rheological profiles (see schematic example in FIG. 1), in different shear requests, occurs in a simultaneous manner. Therefore, one only rheometry test provides subsidies for defining the adequation of compositions to the proposed application methods.

The use of rheometers has enabled a better comprehension of factors that affect the behavior of cementitious materials. FIG. 4 presents the example of one schematic based on the paper by 'Banfil 2005', on the impact of different contents of water, air, microsilica (ultrafine particles) and dispersant on the viscosity and the mortars yield strength.

As observed, the increase of water and dispersant, represented by the sense of arrows, result in the decrease of both rheological parameters. However, the increase in air content practically does not affect the yield strength, in spite of a large impact on viscosity. At last, the increase in microsilica content reduces the viscosity, but it increases the yield The use of the rheometry technique allows a detailed comprehension of the impact that each of the components has on the behavior of concretes in fresh state. Therefore, this characterization tool is fundamental for the preparation of a formulation methodology based on microstructural/rheological concepts.

However, all the pieces of equipment describe present some limitations, such as the rheometers 'Com Tee BML viscometer', 'Cemagref-IMG', 'Two-Point rheometer', 'Btrheom', 'IBB rheometer', portable rheometer and 'Icar' rheometer dedicated to a single family of tests, being comprised of a single set of container and shear geometry.

Another drawback is due to the fact that the mobile rheometers are not rigid, resulting in inaccurate measurements.

Another drawback is due to the fact that the existing rheometers do not have a system for compensating segregation, and, therefore, they do not allow the execution of long-term tests.

Another drawback is due to the fact that commercially available rheometers are developed for the assessment of concretes with fluid consistency or mortars that are not plastic.

Another drawback is due to the fact that the existing rheometers do not have a system for compensating segregation, and, therefore, they do not allow the execution of long-term tests.

Another drawback is due to the fact that commercially available rheometers are developed for the assessment of concretes with fluid consistency or mortars that are not plastic.

Another drawback is due to the fact that the existing pieces of equipment do not act in concretes that require high levels of torque, as dry materials.

Another drawback is due to the fact that the commercially available pieces of equipment are not able to mix materials.

Another drawback is due to the fact that conventional rheometers do not allow the adaptation of devices for mechanical tests.

STATE OF THE ART ANALYSIS

In a research made in specialized databases, some documents related to rheometers were found, such as the document no. PI 0107975-1, which is about methods for studying the properties of a fluid and for producing an extruded polymer, revealing a device for studying the properties of a fluid, polymer production plan, method and device for monitoring one transition from a first product specification to a second product specification in a polymerization process, and, polymer product.

In this state of the art document, one rheometry method and its corresponding device, with the particular application of polymer manufacturing, are revealed.

This method is performed with the purpose of studying the properties of a polymer by means of a rheometer, with a pump and an array disposed in a way that the polymer is pumped through the array with the aid of transducers that measure pressures inside the rheometer.

In this method, the polymer is supplied to the rheometer, and the pump is set at a speed and value(s) that are indicative of the shear strength in the fluid inside the array, obtained by means of transducers that provide data.

The pieces of data are then directly compared, with the use of multivariate analysis with the data previously obtained, which correspond to polymer(s) with known rheological properties.

The results of this comparison can then be used for controlling the manufacturing process.

The document no. PI 9907518-0 refers to a polymeric material morphology visualization device for rotational rheometers, in which the system allows the visualization of the morphology evolution of immiscible polymer blends, or fiber-reinforced polymers, submitted to shear flows in the linear viscoelasticity or nonlinear viscoelasticity regime.

This piece of equipment is comprised of a lighting system, with one mercury vapor lamp which beam is collimated by a set of lenses and deviated by a mirror so as to focus on the sample.

This piece of equipment also includes a morphology visualization system, with one mirror placed under the bottom shearing element of a camera with microscopic lens that allows up to 1000× magnification, enough to visualize morphology to which the size of the disperse phase is coupled to a digitalization device in a microcomputer.

During the polymer deformation test the light beam is transmitted through the sample following the optical path.

The system allows the visualization of the morphology evolution of immiscible polymer blends, or reinforced polymers during shear flows known in the linear viscoelasticity or nonlinear viscoelasticity, just as the verification of non deformation of the morphology of blends submitted to flows that correspond to linear viscoelasticity.

Another document numbered PI9816066-4 reveals one rheometer of double winding extension, which comprises one transmission shaft, connected to an enclosure, where the enclosure is additionally connected to a torque shaft, and two rotating drums are mounted onto the enclosure.

The ends of a sample are connected to each drum and the drums are rotated, stretching the sample until it breaks. The torque on the equipment caused by the stretching of the sample is measured. The environmental control can be produced for testing samples under different conditions.

PURPOSES OF THE INVENTION

With the purpose of presenting improvements to the consumers market, the applicant has developed a universal machine for rheological and mechanical tests for modular tests of cementitious materials, such as mining, asphaltic and polymeric materials, foods, pharmaceutical products, cosmetics, etc.

The aforementioned machine adopts concepts of speed and rotation direction control, torque control and especial modular architecture that are combined in order to comprise a universal machine for rheological and mechanical tests for the assessment of rotational shear forces, as well as the inclusion of a load cell optional device for recording longitudinal forces perpendicular to the rotation direction.

The modular architecture is basically comprised of:
a) Organizational structure made in aluminum and hard steel, free from vibrations and torsion during tests, essentially comprised of a base provided with fastening points and four anti-vibration stands and at least one pan lock, as well as one support to the pan. This base also has a platform elevator, which slides in guide columns attached to the base, with the opposite ends of each guide column equipped with fastening members of an upper lock.
b) Electronic system housed in an electronic components cabinet;
c) Dry gear reducer without oil lubrication;
d) Alternate current servomotor;
e) Fast coupling system for changing geometries and test containers;
f) Set of distinct shear elements with variable geometries for the execution of rheological tests;
g) Fast coupling system able to withstand devices for the performance of mechanical tests with hardened materials;
h) Test containers with different geometries and volumetric capacities;

i) Transportation system of equipment and test containers;
j) Electronic system for speed control, torque control and rotation direction;
k) Load cell device for recording regular longitudinal forces;
l) Modular test software for speed control, torque control and rotation direction;
m) Result analysis software;
n) Electronic system and software for submitting test results for remote analysis;
o) System for the acquisition of ambient temperature and temperature at the test container.

Such configuration allows the assessment of particulate materials in dry conditions, identifying properties as friction between particles, compaction capacity, presence of moisture, etc., as well as systems with the presence of liquid phase, both pure and combined in emulsion and suspension forms, being able to assess since the component mixing and combination to the consolidation of these systems in case of reactive materials.

As it assesses the rotational shear behavior, the rheometer is also able to analyze the rheological behavior in any system that is being sheared.

Therefore, the main advantage of the innovative machine is the junction of two distinct modules that allow different combinations of accessories and software in order to comprise the assessment of rotational shear forces of suspensions and granular material with a wide range of granulometry and consistencies, rendering the machine completely customizable to different families of materials and applications.

Another advantage is due to the fact that the execution of mechanical tests in combination with rheological tests provides a degree of originality that is not found in equipment for high torque tests. Therefore, it is now possible to infer that the current invention extends the concept of rheological tests in heterogeneous multiphase suspensions to a range of tests that had never been previously performed, even including the possibility of combining mechanical to rheological tests.

Another advantage is due to the fact that the provision of a fast-action type coupling system allows the installation of different accessories, being possible to mount mechanical claws for supporting and assessing materials in hardened state.

Another advantage is due to the fact that the machine allows the dry assessment of particulate materials, identifying properties such as friction between particles, acting as a tribometer; assessing the compaction capacity with or without moisture, in systems that have liquid phase, both pure and combined in emulsion and suspension forms, able to assess since the component mixture and combination stage up to the consolidation of these systems in case of reactive materials.

Another advantage is due to the fact that the modular architecture of the universal machine allows its use in different segments, such as in the area of cementitious materials as cement, concretes, mortars, as well as mining, asphaltic and polymeric materials, foods, pharmaceutical products, cosmetics, etc.

Another advantage is due to the fact that the constructiveness of the universal machine ensures its mobility, also encouraged by the provision of use in combination with a transportation device (utility cart) that can carry the machine and be used for the collection of test material, given that the base predicts a fast coupling system of test pans, reducing the effort of moving test containers, especially at locations that are far from the equipment, considering that the estimate weight of recipients supplied with material reaches 60 kg.

Therefore, the use of a utility cart gives mobility to the machine, practicality for the collection of samples, and it also reduces the work efforts by operators, avoiding issues of hazards to operators caused by handling heavy loads.

Another advantage is due to the fact that the constructive characteristics of the machine allow the torque control and possibility of oscillation during tests, as the result of the rotation direction control, as well as it controls the actuation of the linear actuator for the positioning of the elevating mobile platform during tests.

Another advantage is due to the fact that the full sealing of the universal machine allows its use in aggressive environments in terms of dirty conditions, restricting the ingress of dust particles, besides allowing the equipment to be easily washed with water.

DESCRIPTION OF FIGURES

In order to complement the current description for a better comprehension of characteristics of this invention, and according to a preferable practical execution of this invention, this description is followed by a set of drawings which represents in an exemplified and non limitative manner its functioning:

FIG. 5 represents an exploded view of elements which makes up the innovated rheometer;

FIG. 6 shows an exploded view of the gear reducer assembly;

FIG. 14 illustrates schematic views of different test geometries.

DETAILED DESCRIPTION OF THE INVENTION

Figure 1:
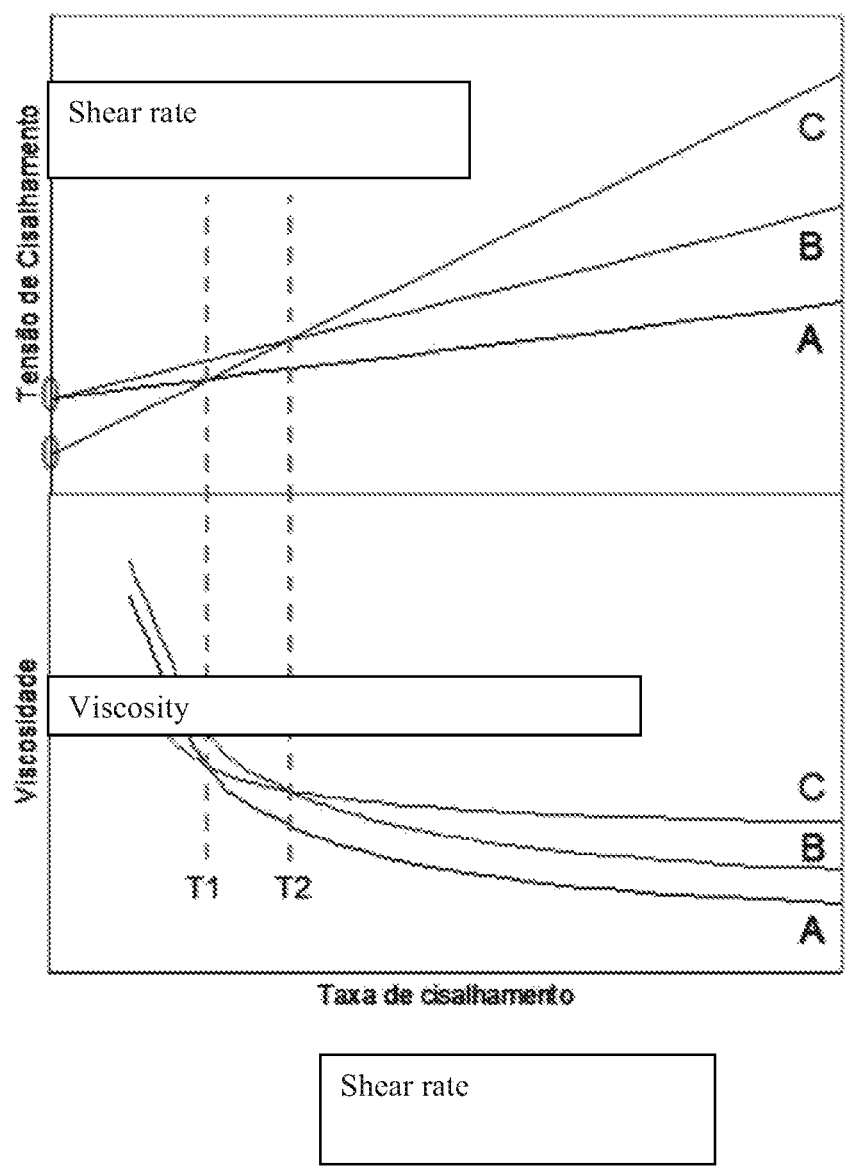
FIG. 1 represents a schematic illustration of the rheological behavior of three distinct. Bingham fluids.
Figure 2:
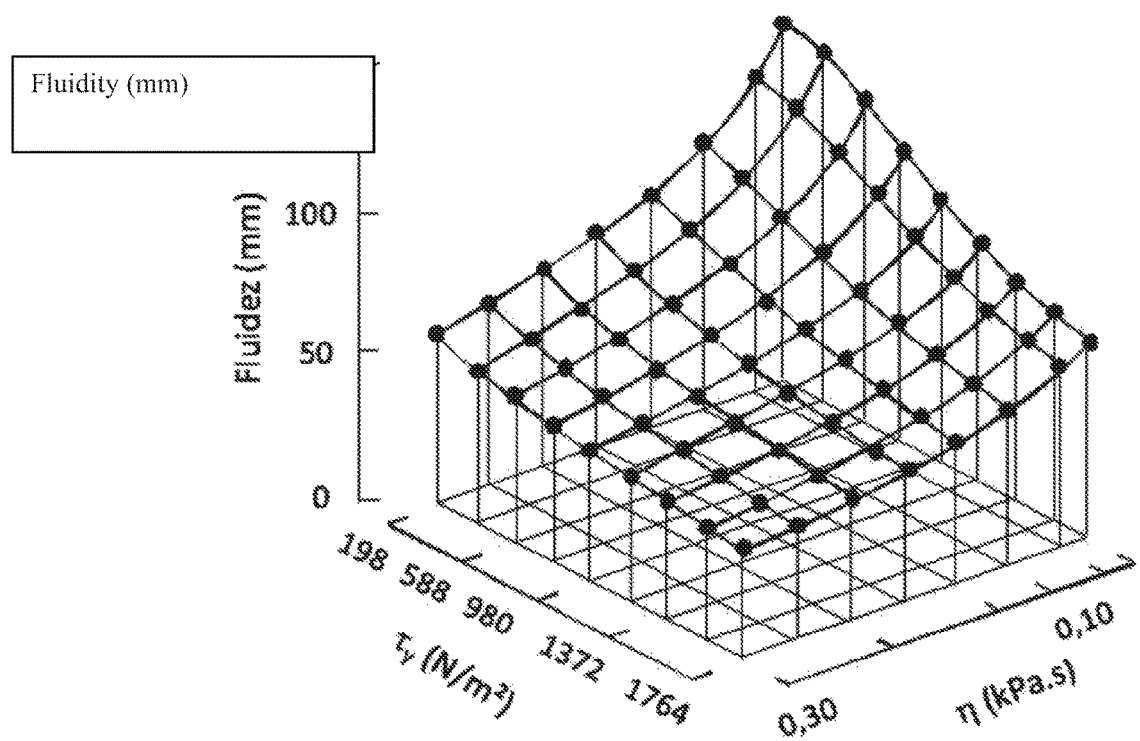
FIG. 2 reveals a graph of the relation between the fluidity value and the rheological constants: yield strength ($\tau_y$) and viscosity ($\eta$)
Figure 3:
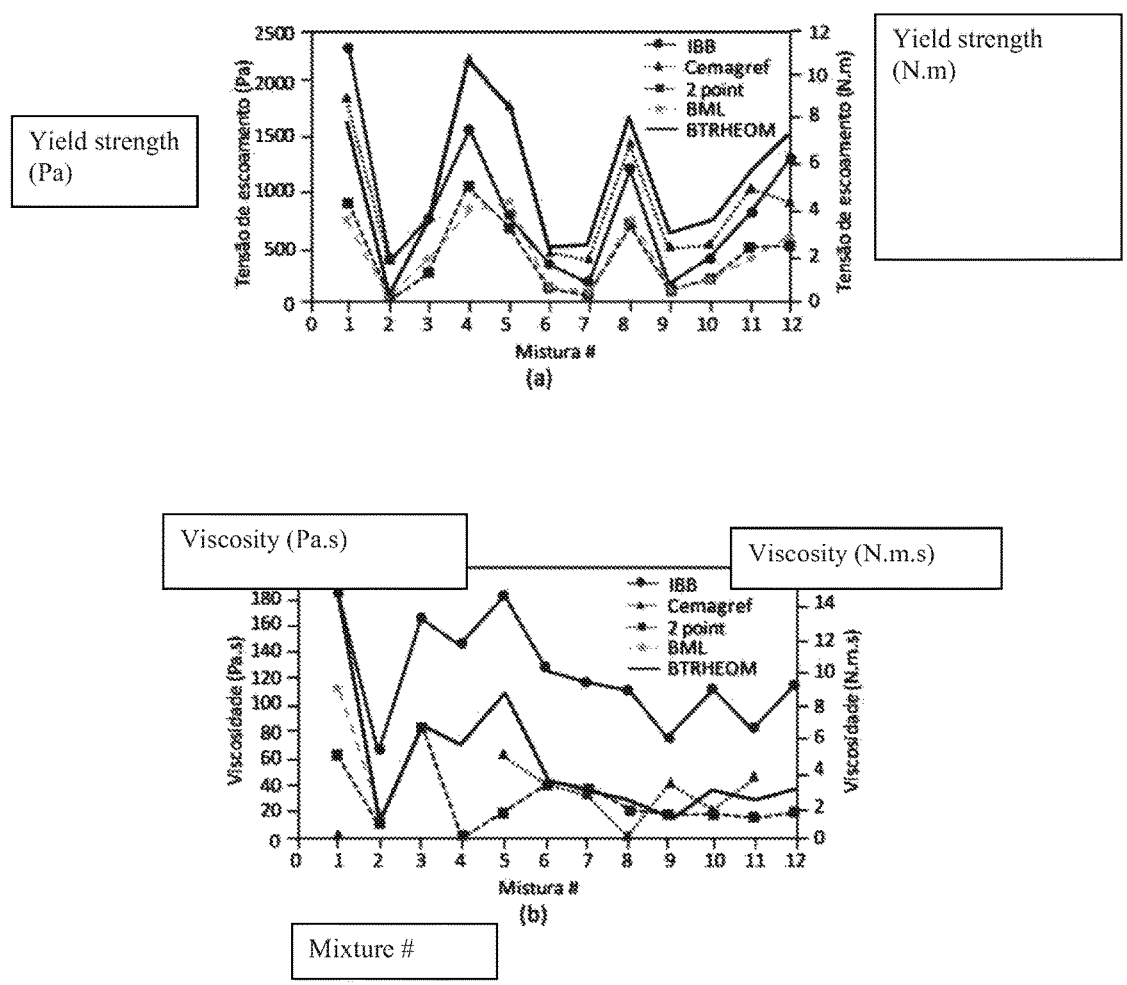
FIG. 3 shows a graph of the yield strength (a) and viscosity (b) of compositions tested in the comparative study of rheometers.
Figure 4:
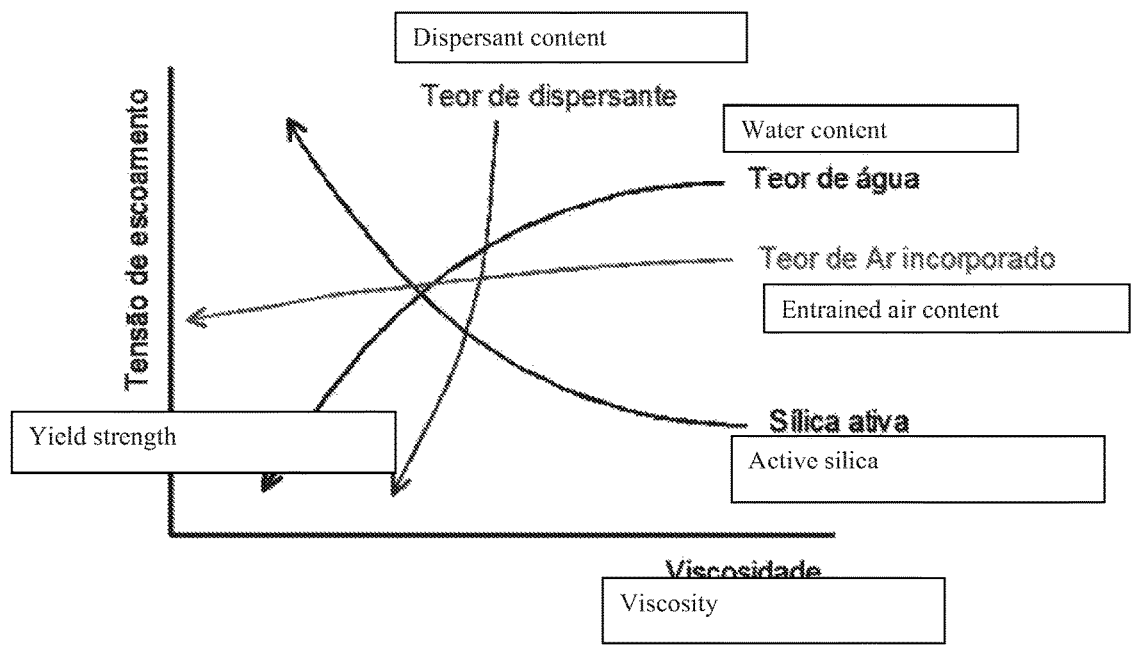
FIG. 4 illustrates a graph based on 'Viskomat NT' rotational rheometry results, related to the impact of different contents of water, air, microsilica—ultrafine particles—and dispersant on the vis and yield strength of mortars. The arrows indicate increases in parameters—Banfill, 2005.
Figure 7:
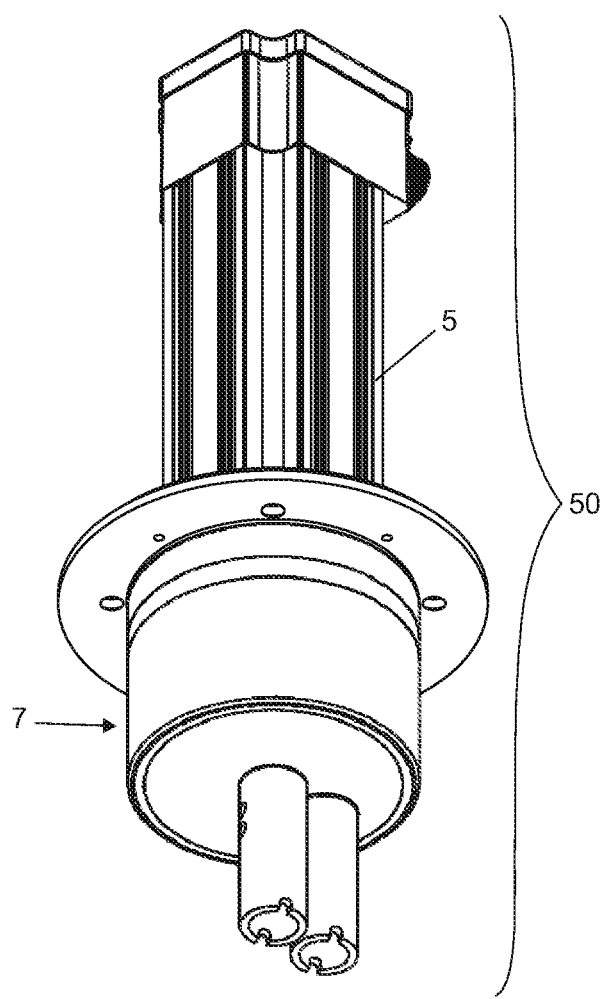
FIG. 7 illustrates an assembled view of the gear reducer assembly.
Figure 8:
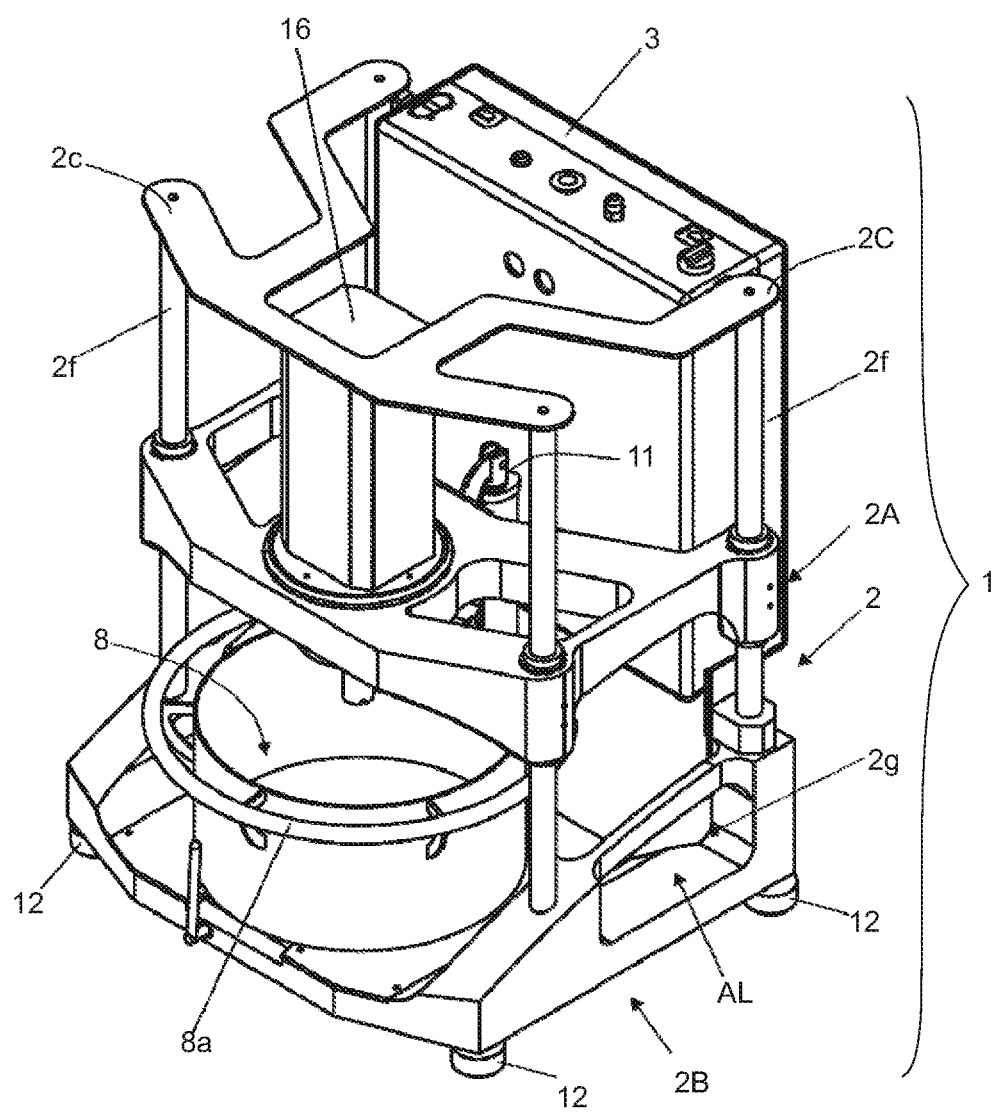
FIG. 8 reveals an assembled view of the innovated rheometer.
Figure 9:
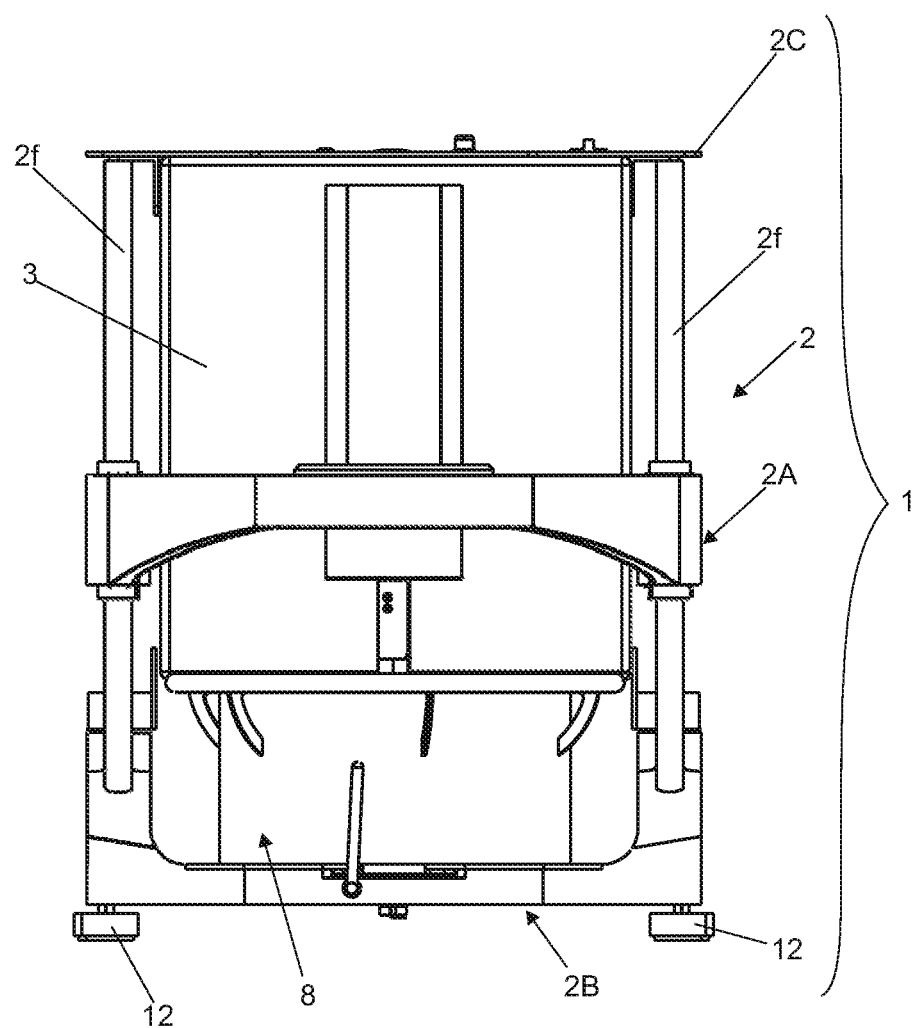
FIG. 9 shows a front view.
Figure 10:
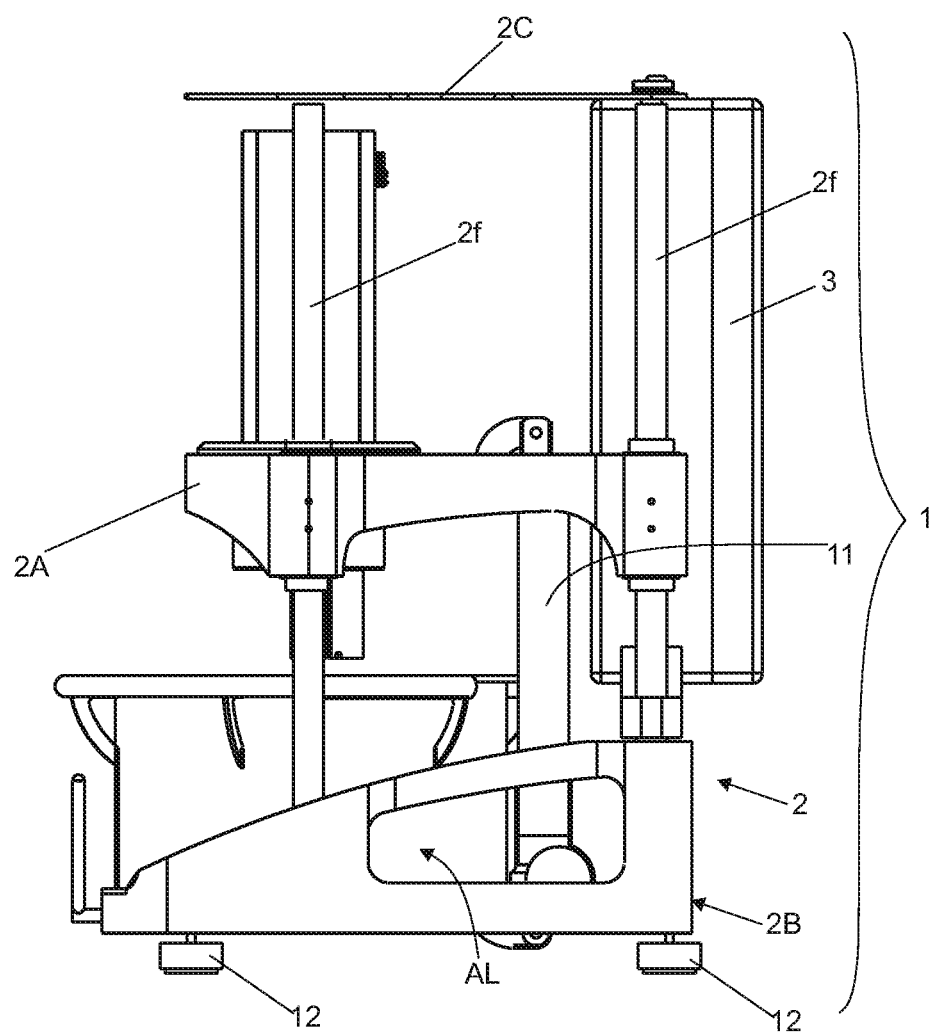
FIG. 10 shows a side view.
Figure 11:
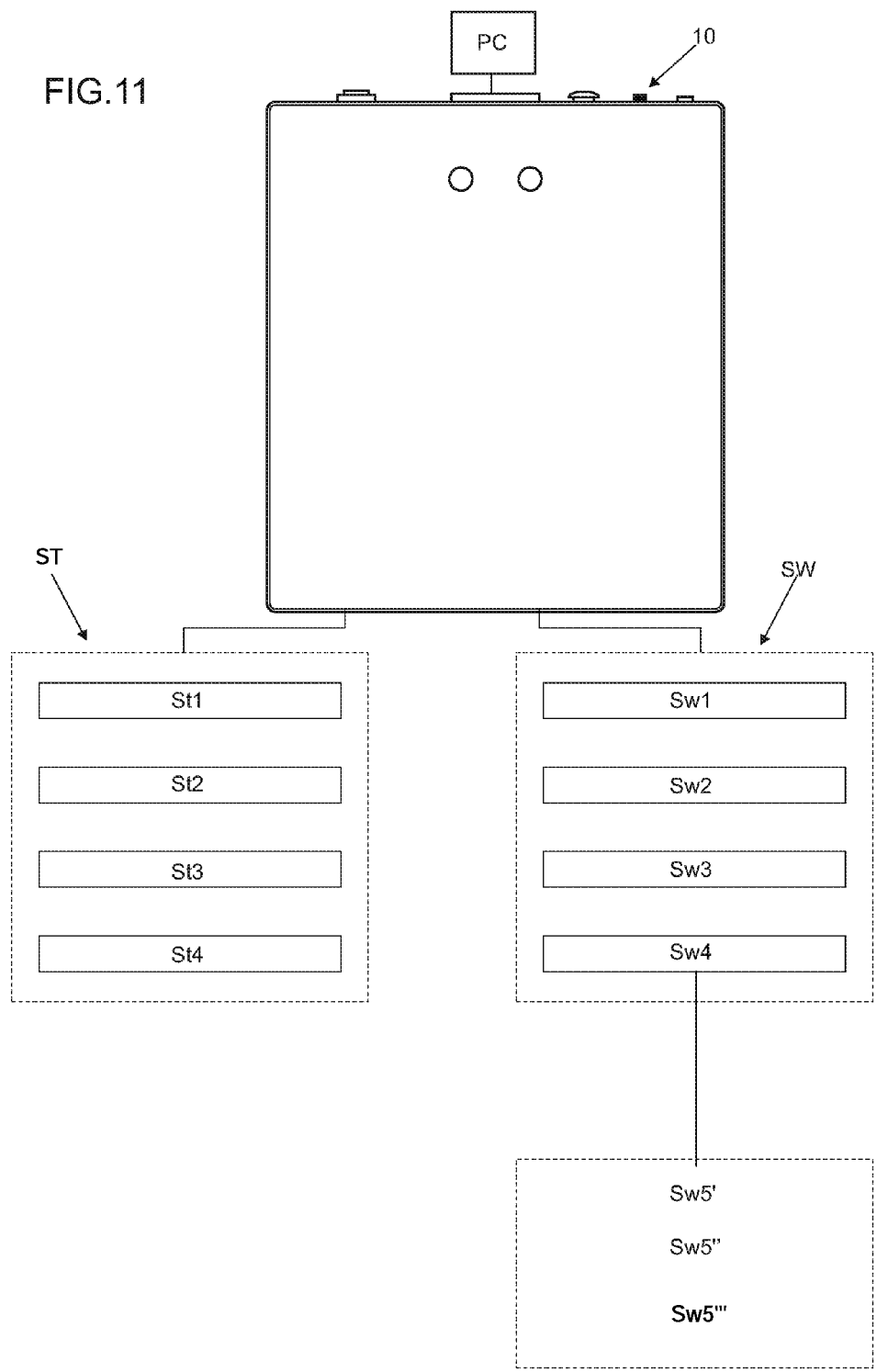
FIG. 11 represents a front view of electric control panel.
Figure 12:
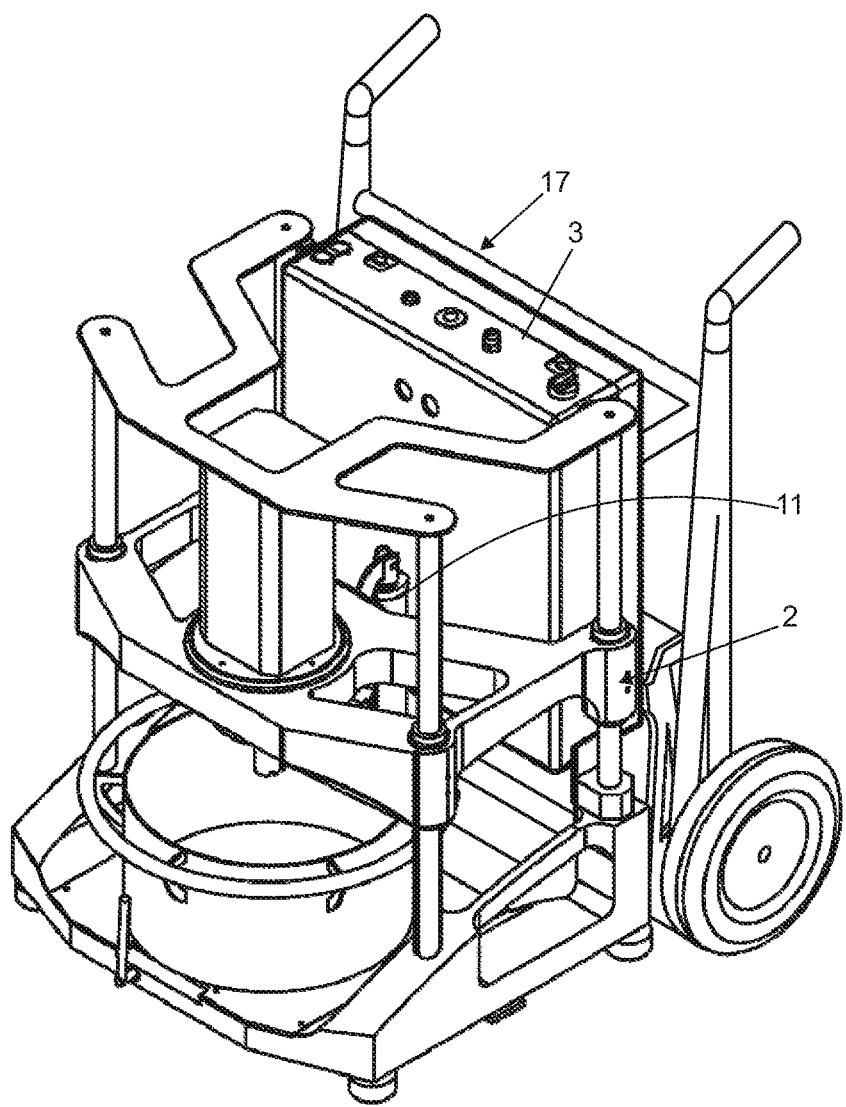
FIG. 12 illustrates a perspective view of the coupled rheometer on the utility cart.
Figure 13:
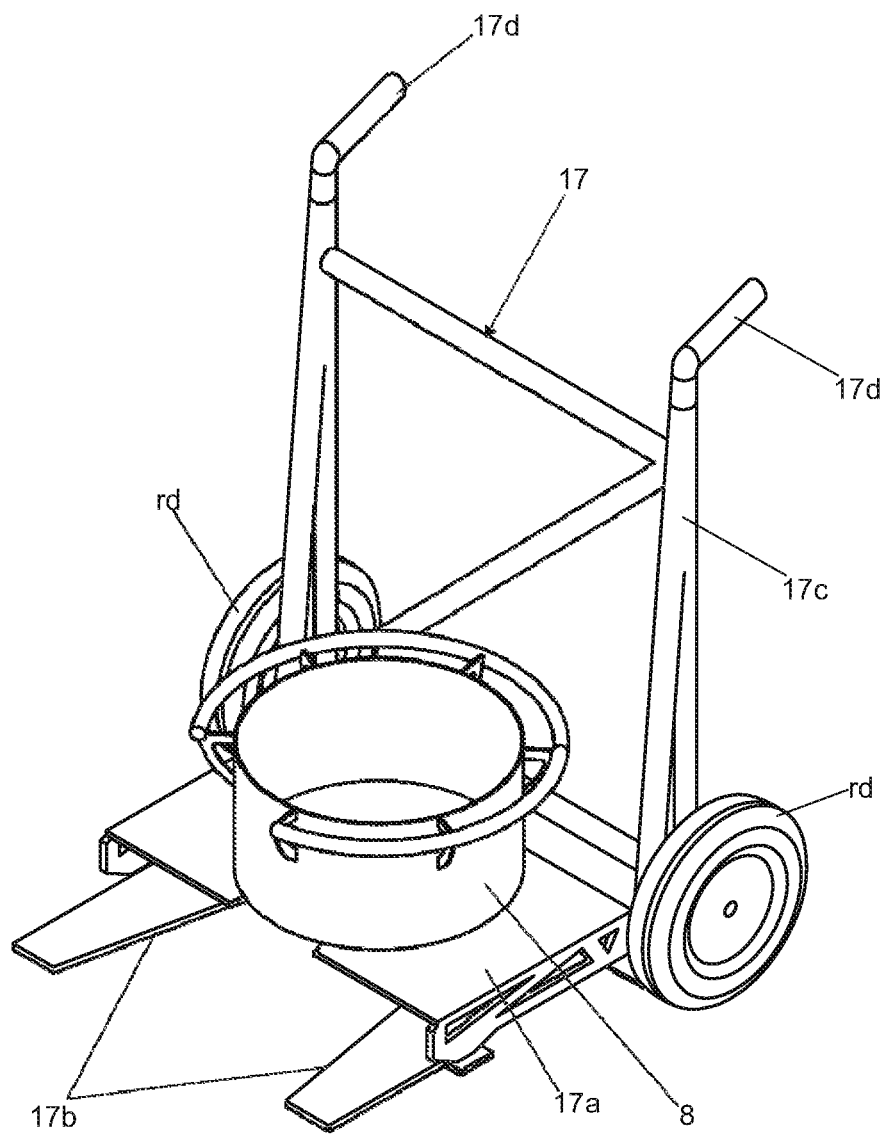
FIG. 13 shows a perspective view of the utility cart transporting the test container.

In reference to the illustrated drawings, the current invention patent refers to the "UNIVERSAL MACHINE OR RHEOLOGICAL AND MECHANICAL TESTS", which is, more precisely, an universal machine (1) of rheological and mechanical tests for modular tests of cementitious materials, as well as mining, asphaltic and polymeric materials, foods, pharmaceutical products, cosmetics, etc.

According to the current invention, the universal machine (1) comprises the arrangement of a set of modules (CM) that make up means of rheological and mechanical tests for the assessment of rotational shear forces, as well as recording of longitudinal forces perpendicular to the rotation direction of the gear reducer assembly (50), considering that these modules (CM) are comprised of: a) structural organization (2); b) electronic components cabinet (3) of the electronics system (St)/(Sw); c) dry gear reducer (4); (d) alternate current servomotor (5); e) fast coupling system (Eg) for changing geometries (18); f) test containers (8), as well as devices for the execution of mechanical tests with hardened materials; g) load cell type device for recording the regular longitudinal forces.

The aforementioned machine (1) provides the interconnection with a data processing system (PC) and the aforementioned modules (CM) are controlled by a specific electronic system (St) for speed control, torque control and rotation direction. This electronic system (St) is comprised of specific subassemblies, which are:

Servoconverter (St1), preferably the model SCA06, manufactured by WEG, compatible with the gear reducer assembly (50) used;

Electric components (St2) for supplying electric current and protection against sudden voltage variations of the servoconverter (St1) that controls the alternate current servomotor (5) and the linear actuator (11) that moves elevating mobile platform (2A) provided for the structural organization (2);

Electronic components (St3) for control and acquisition of movement data of the alternate current servomotor (5) and linear actuator (11);

Electric control panel (10) installed inside the electronic components cabinet (3), to be provided with an on-off switch (10a), error indicator light (10b) on the servoconverter, emergency shutdown switch (10c), USB connection (10d) and energy supply to the control computer (PC), manual control switch (10e) for controlling the vertical motion of the elevating mobile platform (2A);

Optional Wi-Fi communication system (St4) between the computer (PC) and the electronic components cabinet (3);

Modular control, data acquisition and results analysis software (Sw) for programming the rotation to be used during tests simultaneously to the motion of the elevating mobile platform (2A) and the acquisition of torque forces that result from tests. The aforementioned software (Sw) provides:

i) modular test control system (Sw1) for speed control, torque control and rotation direction of the alternate current servomotor (5);

ii) data acquisition system (S 2) for recording in real time all responses provided by the gear reducer assembly (50), besides controlling the time and temperature measurement system, generating data in exportable format for conventional analysis software, such as Excel, as well as for the results analysis software (Sw3);

iii) results analysis system (Sw3) in which the data recorded by the data acquisition system (Sw2) is analyzed by an exclusive rheological analysis software;

iv) remote data transmission system (Sw4) that works in parallel to the other systems for sending data from testing locations to computers located in specific locations;

v) complementary systems (Sw5) that can be coupled to the machine (1) and, consequently increase the scope and effectiveness during the service.

In the ideal constructive version, the complementary system S presents:

Defined location (Sw5') for the installation of a load cell at the supporting base (2B) of the test container (8) for recording the regular longitudinal forces during tests;

Temperature acquisition system (Sw5") for acquisition of temperature at four different positions: position on the gear reducer assembly (50); position on the electronic components cabinet (3) of the electronics system (St)/(Sw); position on the environment; position on the test container (8).

Mechanical testing systems (Sw5''') for materials in hardened state. The structural rigidity of the machine (1) allows the execution of mechanical tests in devices to be coupled to the center shaft of the planetary system and to the fast coupling system (Eg) of the die cast base. Therefore, various testing systems can be conceived for the execution of tests where the vertical motion of the elevating mobile platform (2A) generates vertical forces to be recorded by the load cell.

In an ideal constructive version, the structural organization (2) is preferably made of aluminum and hard steel or other suitable material, being comprised of three main subassemblies, which are: base (2B), elevating mobile platform (2A) and locking element (2C) of the assembly. The aforementioned base (2B) (see FIG. 5A) is ribbed and has weight relief holes; the transversal section in "U" shape makes up sidewalls (2d) where orifices (2e) were made for fitting guide columns (2f) and sliding the elevating mobile platform (2A), which has its vertical motion made by the linear actuator (11) installed between the base (2B) and the elevating mobile platform (2A).

The interior surface of the base (2B) provides means of coupling a set of anti-vibration stands (12), while the opposite surface receives a supporting plate (13) for the test container (8).

Each side wall (2d) of the base (2) features some cutouts (2g) in order to serve as handles (AL) for transporting the machine (1).

The aforementioned support plate (13) provides a central cutout (13a) for the connection of the fast coupling (Eg) of the container (8) base (2B), and this fast coupling (Eg), made of steel and comprised of a lever (6a) formed by an inverted "L"-shaped tubular profile part, which has its free end (6b) coupled to an orifice of the supporting member (2H) to be provided on this base. The 90° motion of the lever (6a) promotes the release of the container (8) from the support plate (13).

The aforementioned elevating mobile platform (2A) is comprised of a single ribbed part (2i) provided with weight relief holes where the peripheral area of the elevating mobile platform (2A) corresponds to the base area (2B), provided with four extreme cylindrical members (2j) where a pair of linear bearings (14) is mounted, ensuring the vertical sliding of the platform (2A) on the guide columns (2f). These bearings (14) are fastened by elastic rings (15) and an Allen headless screw.

The vertical motion of the elevating mobile platform (2A) on the columns (2f) is obtained by the linear actuator (11) with positioning control made by Hall sensor, commanded by means of an electronic system (St) and software (Sw).

The gear reducer assembly (50) is armored and assembled in a position aligned with the vertical shaft (E1) in a center bore (21) on the base of the elevating mobile platform (2A); the aforementioned gear reducer assembly (50) receives a protection cover (16) and it can be divided into three parts, which are: alternate current servomotor (5), cycloidal gear reducer (4) and planetary gear reducer (7). The alternate current servomotor (5) is supplied with 200V supply voltage, features 7.0 Nm of torque and maximum rotation speed of 3000 rpm, and it provides an electromagnetic brake that is directly coupled to the gear reducer, which, in turn, does not need oil lubrication, as it is comprised of a primary cycloidal reducer (4) with an eccentric bearing coupled to a secondary planetary reducer (7).

The aforementioned secondary planetary reducer (7) provides a center shaft with fast coupling system for changing testing geometries (18), besides a fast coupling system able to support devices for the execution of mechanical tests with hardened materials.

These geometries (18) are, preferably made of stainless steel and can present various formats (see FIG. 14), such as, finned geometry for the 200 mm container, finned geometry for the 400 mm container, parallel plates and DIN fin.

The test containers (8) can present different geometries and volumetric capacities, made of stainless steel and "U"-shaped section which has an ring-shaped handle (8a) in the edge that assists in the transportation, while at the base (8b) there three short cylindrical projections (8c) that assists in the positioning and locking in cutouts (13a) provided to the aforementioned plate (13).

The dimension variation of containers (8) can be the following: 400 mm of inside diameter and 200 mm of height and another model with 200 mm of inside diameter and 200 mm of height, where the choice of containers (8) is related to the size of the largest particle to be tested, with 6 mm for the smaller container and 20 mm for the larger container.

The aforementioned machine (1) is provided with an utility cart (17) so that it can be manually transported to the work place. This cart (17) is comprised of a platform (17a) with projecting arms (17b). This platform (17a) is provided with a pair of wheels (rd), which are mounted on stands (17c). The free ends of these stands are developed into handles (17d) that allow the cart (17) to be guided for the transportation of the machine (1) or containers (8).

Therefore, the constructiveness of the machine, combined with the operational (St) and software (Sw) ensure the simplified operation, which functioning can be divided into the second stages;

a) Transportation and assembly of the machine (1) by means of the utility cart (17) for the test location, which can be a laboratory or at the location of application of concrete, mortar, etc. At the location, the machine (1) must be connected to a three-phase electric power supply, 220 V;

b) The utility cart (17) can then be uncoupled in order to be used for collecting materials at the location of their production, for subsequent analysis by the machine (1);

c) Activation of the machine (1) as the electric power supply is connected. The first task consists in connecting the control computer (PC) by means of the USB connection at the upper part of the electric panel (10). From this moment, the machine (1) can be turned on at the on/off switch (10a), and the computer can be started right after.

d) The control of the machine (1) is performed by means of the software (Sw); and e) Collection of material and test execution tasks are performed by moving the test container (8) up to the point of collection of concrete material, mortar, etc. at the location of production and return to the machine (1) for the execution of tests. After the container (8) is placed on the base (2B) of the machine (1), the defined test geometry (18) is coupled and the test is started by means of the control software (Sw).

Another alternative for performing the test consists in placing the container (8) and test geometry (18) on the machine (1), adding the materials to be tested to the container. That can be done by placing the anhydrous materials so that they can be mixed in the machine (1) or placing the ready material only for analysis at the equipment.

Once tests are completed, the machine software (1) will generate electronic results files that are analyzed by another software specifically developed for handling torque, rotation, time and regular force data. The analysis software provides rheological information from tests and compares results obtained in different tests, besides allowing the assessment of results' compliance with previously defined behavioral standards. It is certain that when this invention is put into operation, certain modifications can be introduced in regards to certain construction and form details, without interfering with the fundamental principles that are clearly substantiated in the context of the claim, thus, being understood that the terminology used was not intended to be limited.

The invention claimed is:

1. An universal machine for rheological and mechanical tests, for modular tests of cementitious materials, mining, asphaltic and polymeric materials, foods, pharmaceutical products and cosmetics, and other applications, comprising:
   an arrangement of a set of modules for assessment of rotational shear forces, and recording of longitudinal forces perpendicular to a rotation direction of a gear reducer assembly, wherein the set of modules further comprises:
   a structural organization;
   an electronic components cabinet of an electronics system;
   a dry gear reducer for changing geometries;
   test containers and devices for performing mechanical tests with hardened materials; and
   a load cell device for recording regular longitudinal forces,
wherein the machine provides interconnection with a data processing center, and
wherein the modules are controlled by a specific electronic system for speed control, torque control and rotation direction, which is comprised of specific subassemblies, wherein the specific subassemblies further comprise:
   a servoconverter compatible with an alternate current servomotor used;
   electric components for supplying of electric current and protection against sudden voltage variations of the servoconverter that controls the alternate current servomotor and a linear actuator that moves an elevating mobile platform provided in the structural organization;
   electronic components for the control and data acquisition of the alternate current servomotor and linear actuator;
   an electric control panel installed in the electronic components cabinet where are to be provided one on-off switch, error indicator light on the servoconverter, emergency shutdown switch, USB connection and power supply to a control computer, manual control switch of vertical motion of the elevating mobile platform;
   an optional Wi-Fi communication system between the control computer and the electronic components cabinet; and a modular software for control, data acquisition and result analysis for programming of rotation to be employed in tests, simultaneously to the vertical motion of the elevating mobile platform and acquisition of torque forces resulting from tests, wherein the modular software provides:

i) modular control system of tests for the speed control, torque control and rotation direction of the alternate current servomotor;

ii) a data acquisition system for recording in real time all responses provided by the alternate current servomotor, besides controlling time and a temperature measurement system, generating data in exportable format to a result analysis software and other conventional analysis software;

iii) a result analysis system in which data recorded by the data acquisition system is analyzed by an exclusive rheological analysis software;

iv) a remote data transmission system that acts in parallel to the data acquisition system for submitting data from test locations to computers located in specific locations; and v) complementary systems that can be coupled to the machine.

2. The machine according to claim 1, wherein the complementary system further comprises:

a defined location for installation a load cell on a support base of a test container for recording regular longitudinal forces during tests;

a temperature acquisition system for the acquisition of temperature at four different positions, comprising:
a position on the alternate current servomotor;
a position on the electronic components cabinet;
a position on an environment;
a position on the test container, and mechanical test systems for materials in hardened conditions, as structural rigidity of the machine allows the execution of mechanical tests on devices to be coupled on a center shaft of the planetary gear reducer and on the fast coupling system of a die cast base.

3. The universal machine according to claim 1, wherein the structural organization is comprised of three main sub-assemblies, comprising:
a base;
an elevating mobile platform; and
a locking element of the assembly,
wherein the base is ribbed and features weight relief holes, wherein a transversal section in "U" shape forming sidewalls, wherein orifices are made for fitting guide columns and sliding the elevating mobile platform, which has its vertical motion made by the linear actuator installed between the base and the elevating mobile platform, wherein a lower surface of the base provides a coupling element of a set of anti-vibration stands and an opposite surface receives a support plate of the test container, wherein each sidewall of the base features cutouts to serve as handles for transporting the machine, wherein the support plate provides a central cutout for connection of a fast coupling of the container and base, and wherein the fast coupling is comprised of a lever formed by an inverted "L"-shaped tubular profile part which has its free end coupled to an orifice of a supporting member provided on the base.

4. The universal machine according to claim 3, wherein the structural organization is manufactured from aluminum and hard steel, and wherein the fast coupling comprises steel.

5. The universal machine according to claim 3, wherein a 90° motion of the lever promotes the release of the container from the support plate, wherein the elevating mobile platform comprises a single ribbed part provided with weight relief holes, wherein a peripheral area of the elevating mobile platform corresponds to the base area provided with four extreme cylindrical members where a pair of linear bearings is mounted for ensuring vertical sliding of the platform on the guide columns.

6. The universal machine according to claim 5, wherein the linear bearings are fastened by elastic rings and an Allen headless screw.

7. The universal machine according to claim 3, wherein the test containers are made of stainless steel and "U"-shaped section which has an ring-shaped handle in an edge that assists in transportation, wherein the base comprises three short cylindrical projections that assists in the positioning and locking in cutouts provided to the support plate, wherein dimension variation of containers comprises: 400 mm of inside diameter and 200 mm of height and another model with 200 mm of inside diameter and 200 mm of height, and wherein the choice of containers is related to a size of a largest particle to be tested, with 6 mm for a smaller container and 20 mm for a larger container.

8. The universal machine according to claim 1, wherein the gear reducer assembly comprises an armored gear reducer assembly, and wherein the gear reducer assembly is assembled in a position aligned with a vertical shaft in a center bore on the base of the elevating mobile platform, wherein the gear reducer assembly receives a protection cover and is divided into three parts, comprising:
the alternate current servomotor;
a cycloidal gear reducer; and
a planetary gear reducer,
wherein the alternate current servomotor is supplied with 200V supply voltage, features 7.0 Nm of torque and a maximum rotation speed of 3000 rpm, and provides an electromagnetic brake that is directly coupled to the gear reducer, and
wherein a secondary planetary reducer provides a center shaft with fast coupling system for changing testing geometries, besides a fast coupling system able to support devices for the execution of mechanical tests with hardened materials.

9. The universal machine according to claim 8, wherein the electromagnetic brake does not need oil lubrication as it is comprised of a primary cycloidal reducer with an eccentric bearing coupled to the secondary planetary reducer.

10. The universal machine according to claim 1, wherein the geometries made in stainless steel that can present various formats comprising: finned geometry for a 200 mm container, finned geometry for a 400 mm container, parallel plates and DIN fin.

11. The universal machine according to claim 1, wherein a utility cart is comprised of a platform with projecting arms, wherein the platform is provided with a pair of wheels which are mounted on stands, and wherein the free ends of the anti-vibration stands are developed into handles that allow the utility cart to be guided for the transportation of the machine or containers.

* * * * *